(12) United States Patent
Hosaka

(10) Patent No.: US 8,808,166 B2
(45) Date of Patent: Aug. 19, 2014

(54) ENDOSCOPE

(75) Inventor: Yoichi Hosaka, Iruma (JP)

(73) Assignee: Olympus Corporation, Tokyo (JP)

( * ) Notice: Subject to any disclaimer, the term of this patent is extended or adjusted under 35 U.S.C. 154(b) by 1309 days.

(21) Appl. No.: 12/146,019

(22) Filed: Jun. 25, 2008

(65) Prior Publication Data

US 2008/0275302 A1 Nov. 6, 2008

(30) Foreign Application Priority Data

Jun. 27, 2007 (JP) ................................. 2007-169283

(51) Int. Cl.
*A61B 1/01* (2006.01)
*A61B 1/005* (2006.01)

(52) U.S. Cl.
CPC .................................. *A61B 1/0052* (2013.01)
USPC ........... 600/146; 600/106; 600/114; 600/139; 600/140; 600/141; 600/142; 600/149; 74/89.22; 604/528

(58) Field of Classification Search
USPC ................. 600/106, 114, 146, 149, 139–142; 74/89.22; 604/528
See application file for complete search history.

(56) References Cited

U.S. PATENT DOCUMENTS

| | | | |
|---|---|---|---|
| 3,394,611 A * | 7/1968 | Beurrier | 74/471 R |
| 3,788,303 A * | 1/1974 | Hall | 600/148 |
| 4,076,218 A * | 2/1978 | Gault | 254/326 |
| 2002/0143238 A1* | 10/2002 | Hino et al. | 600/146 |
| 2003/0092965 A1* | 5/2003 | Konomura et al. | 600/146 |
| 2006/0069311 A1* | 3/2006 | Sullivan et al. | 600/149 |
| 2008/0018211 A1* | 1/2008 | Dye | 312/223.3 |

FOREIGN PATENT DOCUMENTS

| | | |
|---|---|---|
| JP | 2003-325437 | 11/2003 |
| JP | 2004-321492 | 11/2004 |
| JP | 2005-013613 | 1/2005 |

* cited by examiner

*Primary Examiner* — Matthew J Kasztejna
*Assistant Examiner* — Kevin G Barry, III
(74) *Attorney, Agent, or Firm* — Dickstein Shapiro LLP

(57) ABSTRACT

An endoscope includes an endoscope insertion portion having a bendable bending portion and a bending mechanism configured to bend the bending portion. The bending mechanism includes a pulley, at least one annular member, a pulling member, and a pulling operation member. The pulley is rotatably driven. The annular member is formed into a C-shape with a cut-out, and can be elastically deformed. The annular member is externally fitted to the pulley with a gap. The pulling member has an intermediate portion wound around the annular member. The distal end portion of the pulling member is connected to the bending portion, and the proximal end portion of the pulling member is connected to the pulling operation member which pulls the pulling member. The width direction position at the winding start position of the pulling member wound around the annular member is made different from the width direction position at the winding end position of the pulling member.

21 Claims, 14 Drawing Sheets

ENDOSCOPE

CROSS REFERENCE TO RELATED APPLICATION

This application claims benefit of Japanese Application No. 2007-169283 filed in Japan on Jun. 27, 2007, the contents of which are incorporated by this reference.

BACKGROUND OF THE INVENTION

1. Field of the Invention

The present invention relates to an endoscope which includes an endoscope insertion portion having an actively bendable bending portion.

2. Description of the Related Art

In recent years, in various fields such as the medical field and the industrial field, there has been utilized an endoscope having a long length endoscope insertion portion inserted into a subject. Such endoscope includes a type in which a bendable bending portion is provided on the distal end side of the endoscope insertion portion, and a bending mechanism for actively bending the bending portion is provided on the proximal end side of the endoscope insertion portion.

For example, in Japanese Patent Application Laid-Open Publication No. 2005-13613 (hereinafter referred to as Document 1), there is proposed an endoscope which includes, as the bending mechanism, a pulley rotated by a driving portion, an annular member rotatably arranged on the outer peripheral surface side of the pulley, and a pulling member whose intermediate portion is wound and arranged around the annular member in a state of being wound substantially one time, whose distal end portion is fixed to a bending portion, and whose proximal end portion is fixed to an operation portion.

In the endoscope having such bending mechanism, when the proximal end portion of the pulling member is pulled by the operation portion, the pulling member, which is wound around the annular member about one time, is hence pulled and moved so as to reduce the diameter of the annular member. Thereby, the annular member is brought into close contact with the pulley, so as to be rotated together with the pulley. As a result, the distal end of the pulling member is pulled and moved by the rotation of the pulley, so that the bending portion is bent in a predetermined direction.

However, in the bending mechanism of the endoscope as described in Document 1, when the pulling member is pulled and moved as described above, a portion of the pulling member which is extended from the operation portion and starts to be wound around the annular member, may be rubbed with a portion of the pulling member which is extended to the bending portion from the state of being wound around the annular member about one time.

SUMMARY OF THE INVENTION

An endoscope according to the present invention includes an endoscope insertion portion having a bendable bending portion, and a bending mechanism configured to actively bend the bending portion. The bending mechanism is configured by including a pulley, at least one annular member, a pulling member, and a pulling operation member. The pulley is driven and rotated. The annular member is formed into an approximate C-shape having a cut-out, and is elastically deformable. The annular member is externally fitted to the pulley so as to have a slight gap with the pulley. The intermediate portion of the pulling member is wound around the annular member. The distal end portion of the pulling member is connected to the bending portion of the endoscope insertion portion, and the proximal end portion of the pulling member is connected to the pulling operation member configured to pull the pulling member. The pulling member is arranged in such a manner that the position in the width direction at the winding start position of the pulling member which is wound around the annular member, is different from the position in the width direction at the winding end position of the pulling member which is extended to the bending portion from the state being wound around the annular member.

The above and other objects, features and advantages of the invention will become more clearly understood from the following description referring to the accompanying drawings.

DETAILED DESCRIPTION OF THE PREFERRED EMBODIMENTS

In the following, embodiments according to the present invention will be described with reference to the accompanying drawings.

Figure 1:
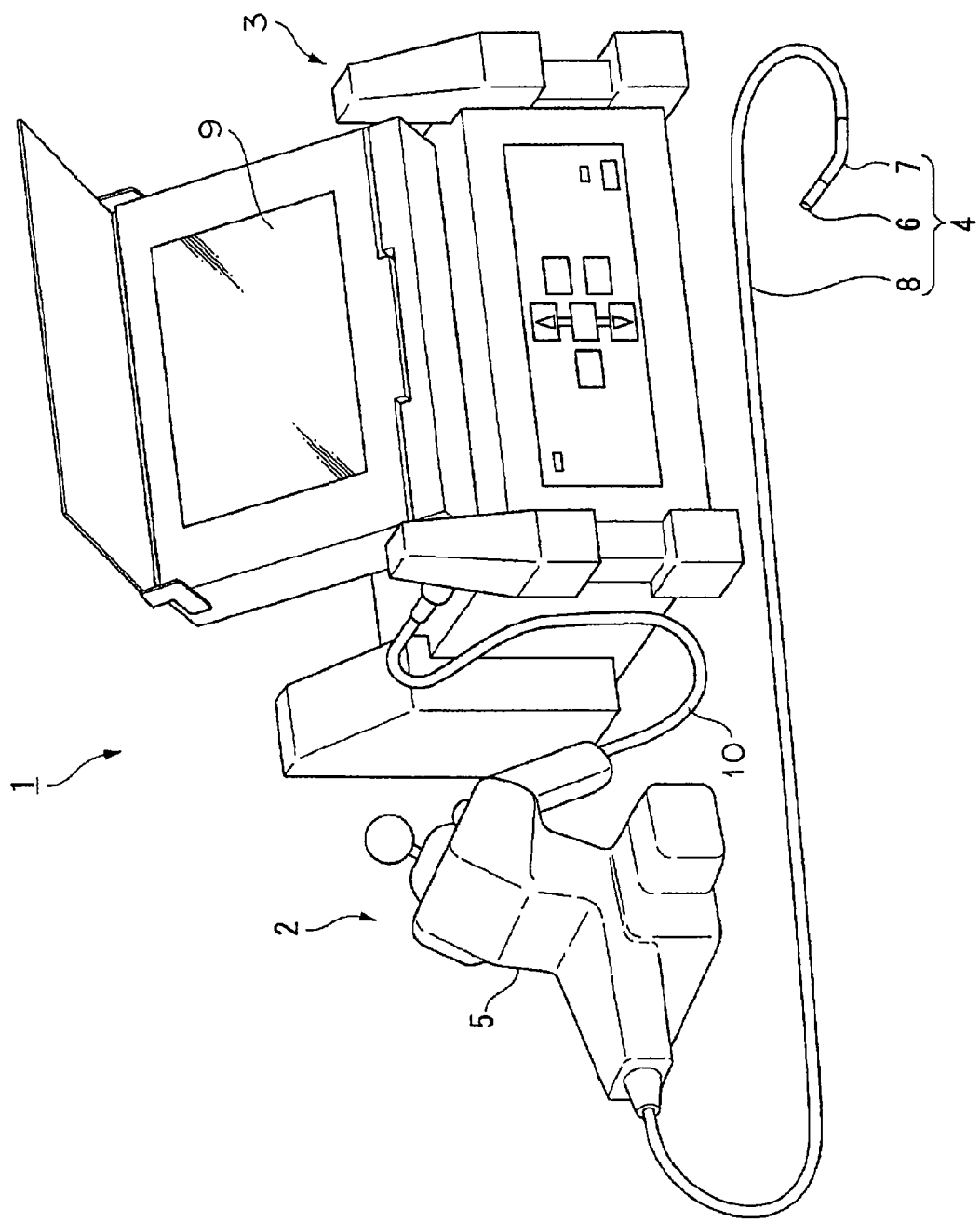
FIG. 1 is a view showing an entire configuration of an endoscope apparatus having an endoscope according to an embodiment of the present invention.

FIG. 1 shows an endoscope apparatus 1 used in the industrial field. The endoscope apparatus 1 shown in FIG. 1 is mainly configured by an endoscope 2 for observing an object, and an apparatus main body 3 which processes and displays an image obtained from the endoscope 2.

The endoscope 2 is configured by a thin and long flexible endoscope insertion portion 4 which is inserted into the object, and an operation portion 5 which is connected to the proximal end portion of the endoscope insertion portion 4, and operates the endoscope insertion portion 4 (a bending portion 7 as will be described below). The endoscope insertion portion 4 is configured by providing successively from the distal end side, a distal end portion 6 in which an image pickup device and a lighting element (both not shown) are incorporated, the bendable bending portion 7, and a thin and long flexible tube portion 8. As the image pickup device incorporated in the distal end portion 6, for example, a CCD or a C-MOS (complementary metal oxide semiconductor) is used. Also, a light emitting diode, or the like, is used as the lighting element. The bending portion 7 is configured by successively providing nodal rings (not shown), so as to be bendable in a predetermined direction. The bending portion 7 according to the present embodiment is configured so as to be bendable in the four vertical and horizontal directions.

The apparatus main body 3 incorporates therein a camera control unit (hereinafter abbreviated as CCU) which is a communication control apparatus for performing processing of signals from the image pickup device provided in the distal end portion 6 of the endoscope 2, or a recording apparatus for storing the processed image. The apparatus main body 3 also includes a monitor 9 which displays the processed image. The apparatus main body 3 is connected to the operation portion 5 of the endoscope 2 via a universal cable 10, so that the image signal from the image pickup device is transmitted to the CCU incorporated in the apparatus main body 3, via the universal cable 10. It is configured such that the CCU converts the image signal into a TV signal and then transmits the TV signal to the monitor 9.

Figure 2:
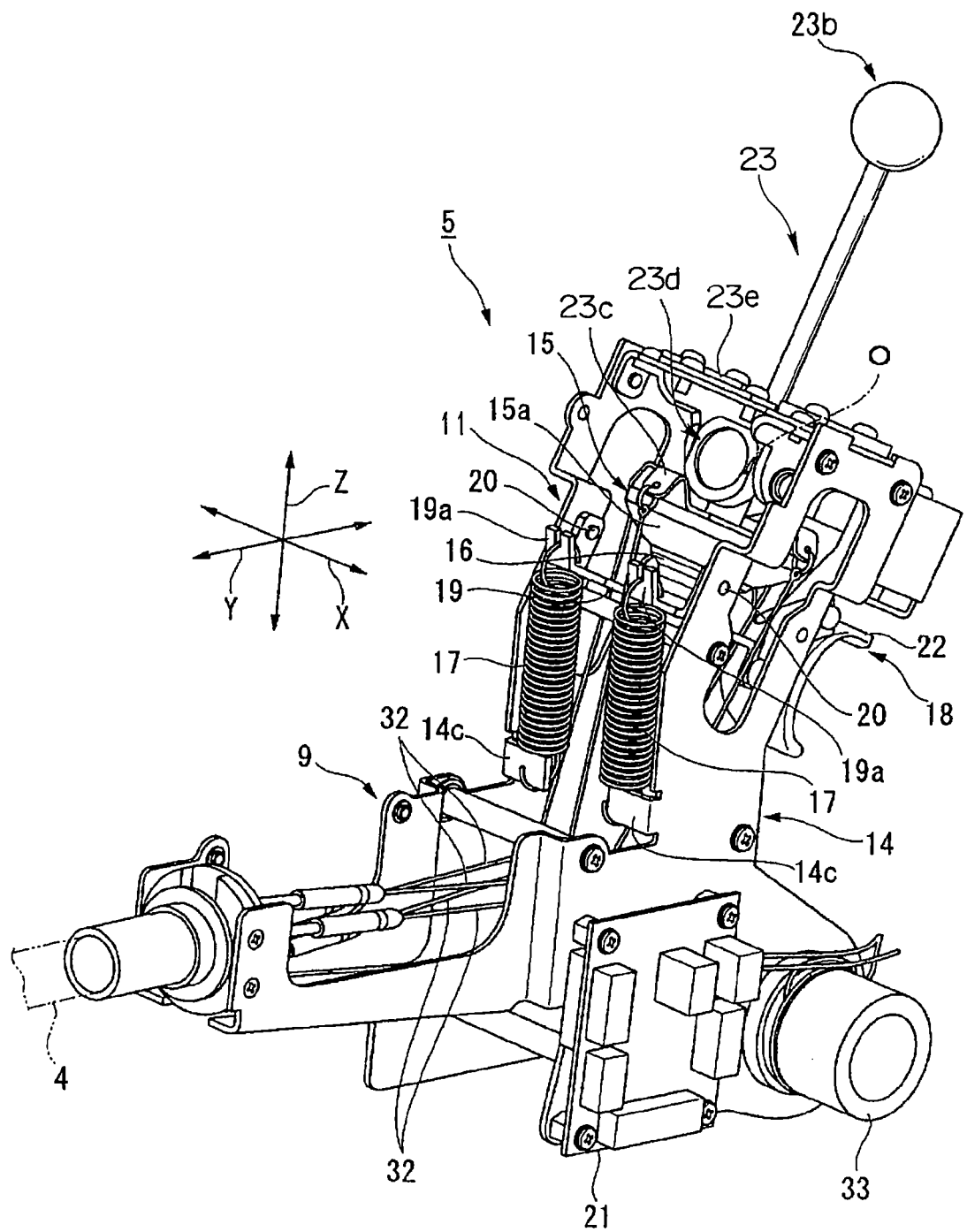
FIG. 2 is a detail view showing an internal configuration of an operation portion of the endoscope.

In the present embodiment, the X direction shown in FIG. 2 is assumed as the right and left direction, the Y direction shown in FIG. 2 is assumed as the front and rear direction, and the Z direction shown in FIG. 2 is assumed as the up and down direction. That is, the direction in which the endoscope insertion portion 4 is connected is the front direction, the direction in which an operation lever 23b (as will be described below) is provided is the upper direction, and the direction in which a substrate 21 (as will be described below) is provided is the left direction.

In the operation portion 5 shown in FIG. 2, there are provided a bending mechanism 31 (see FIG. 3) configured to bend the bending portion 7 shown in FIG. 1, and a locking mechanism 11 for fixing the movement of the bending mechanism 31.

Figure 3:
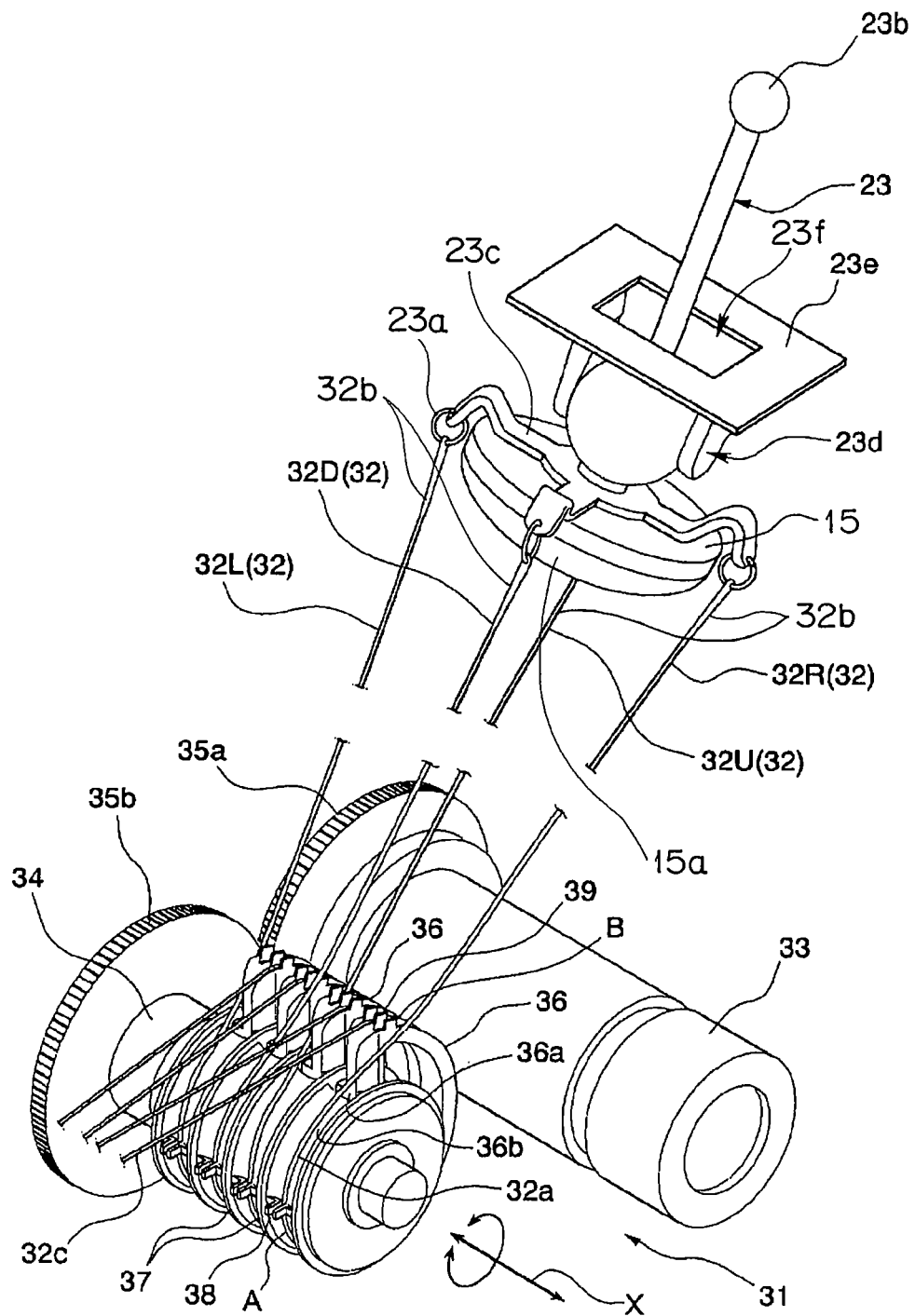
FIG. 3 is a perspective view of a part of a bending mechanism provided in the operation portion of the endoscope.

As shown in FIG. 3, the bending mechanism 31 is configured by including a drive motor 33, a pulley 34 as a shaft body which can be rotated by the drive motor 33, a plurality of annular members 36 which are respectively externally fitted to the pulleys 34 and which are C rings as four rotating bodies in the present embodiment, operation wires 32 which are four pulling members respectively wound around the annular members 36, and a pulling operation member 23 which performs the pulling operation of the operation wires 32.

The drive motor 33 is a drive mechanism which drives and rotates a driving shaft (not shown), and is arranged at the rear end of the operation portion 5 as shown in FIG. 2 and FIG. 3. A first gear 35a is provided to the driving shaft of the drive motor 33. The drive motor 33 is provided through a frame 14 configured by two plate members arranged to face each other, and is fixed to the frame 14.

As shown in FIG. 3, the pulley 34 is arranged in front of the drive motor 33. A second gear 35b which engages with the first gear 35a is provided at one end of the pulley 34, and the pulley 34 is rotated around the shaft by the rotational drive of the drive motor 33. The pulley 34 is arranged in the inside of the frame 14 shown in FIG. 2, and attached to the frame 14.

The each annular member 36 is an elastically deformable member which is formed into an approximate C-shape having a cut-out 36a, and is externally fitted to the pulley 34 in a rotatable manner. The respective annular members 36 are paired with operation wires 32, and are arranged side by side in the X direction which is the axial direction of the pulley 34 and the width direction of the operation portion 5. Further, a substantially annular spacer 37 which is externally fitted to the pulley 34 is provided between the annular members 36.

Figure 4:
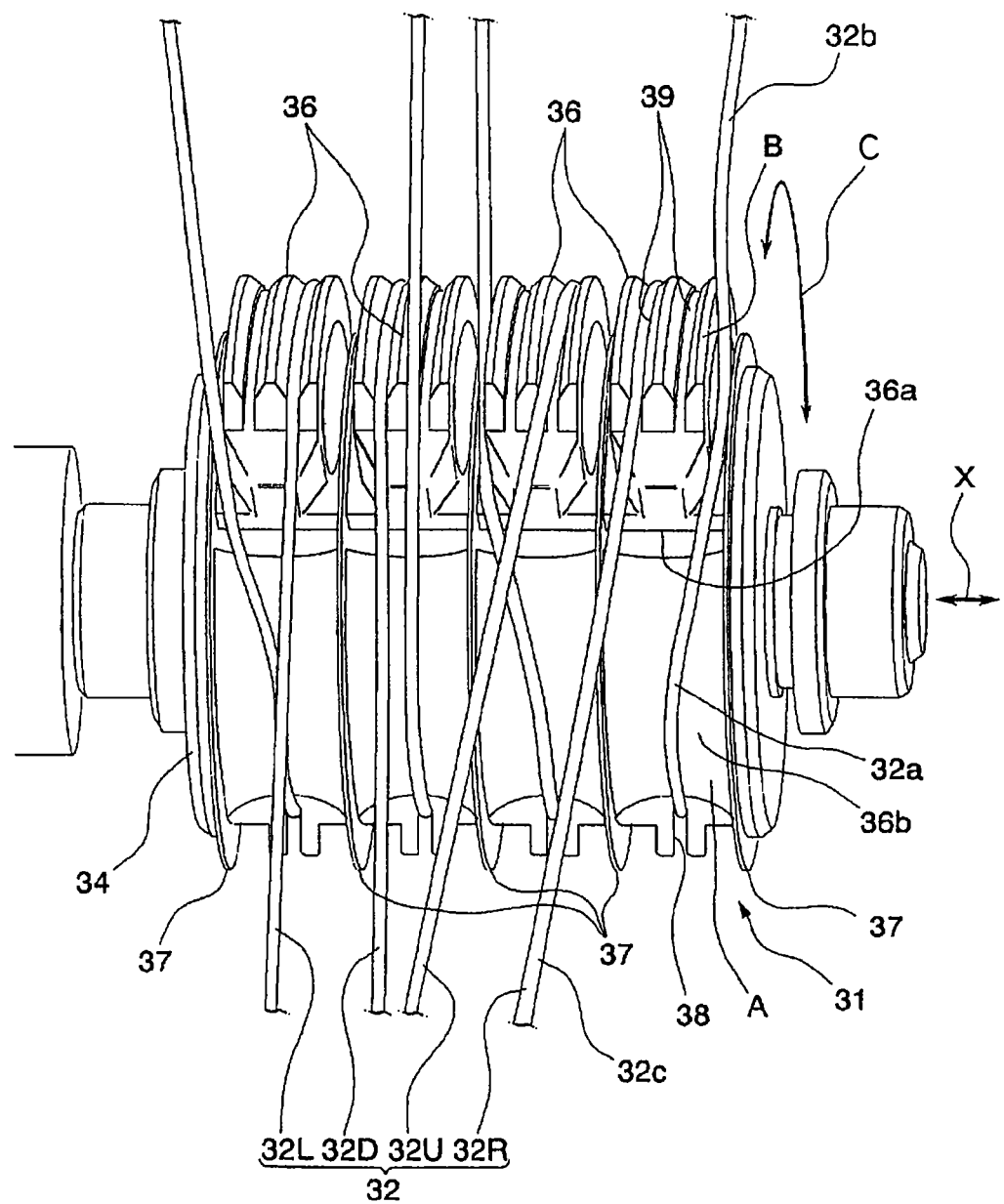
FIG. 4 is an enlarged perspective view showing in detail pulleys and annular members which are provided in the bending mechanism of the endoscope.
Figure 5:
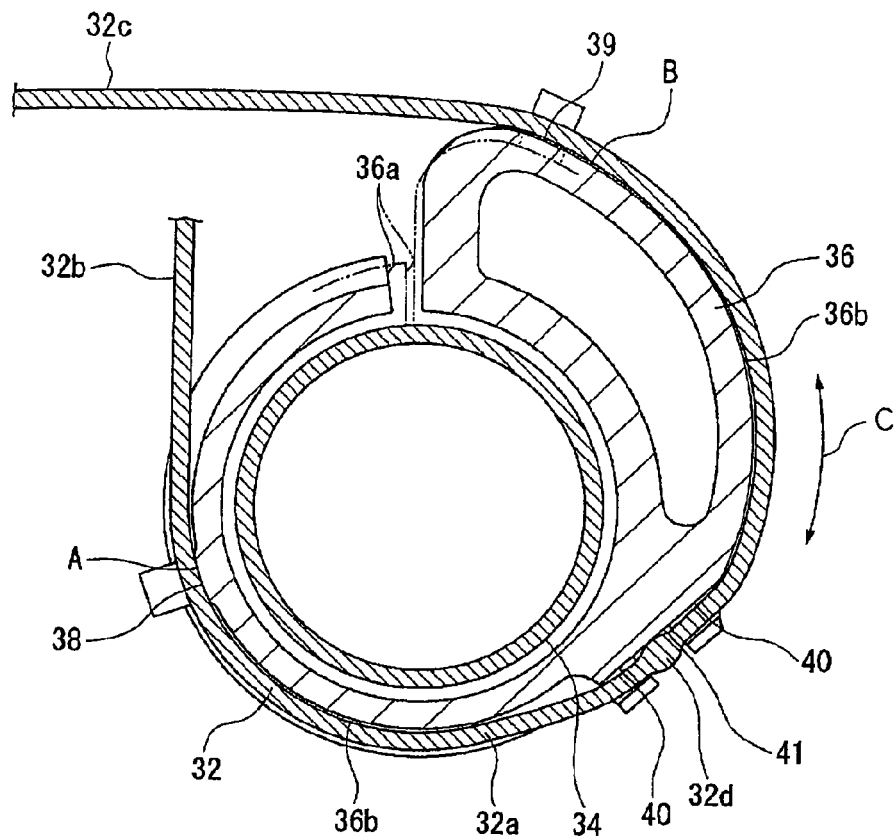
FIG. 5 is a sectional view showing the pulley and the annular member which are provided in the bending mechanism of the endoscope.

As shown in FIG. 3, FIG. 4, and FIG. 5, an intermediate portion 32a of the operation wire 32 is wound around an outer peripheral surface 36b of the annular member 36 which is paired with the operation wire 32. The proximal end portion 32b of the each operation wire 32 is connected to each portion of the pulling operation member 23. On the other hand, the distal end portion 32c of the each operation wire 32 is connected to each of the nodal rings which configure the bending portion 7 in the inside of the endoscope insertion portion 4 shown in FIG. 1.

Further, in the each operation wire 32, the intermediate portion 32a between the proximal end portion 32b connected to the pulling operation member 23 and the distal end portion 32c connected to the nodal ring, is wound around the annular member 36 approximately one time so that the proximal end portion 32b and the distal end portion 32c cross with each other in a side view. Thus, it is configured such that the operation wire 32 can be tightened around the annular member 36 by operating the pulling operation member 23 and pulling the proximal end portion 32b of the operation wire 32.

The above described operation wire 32 will be described in detail.

As shown in FIG. 3, the operation wires 32 are configured by four wires of an upward operation wire 32U, a downward operation wire 32D, a leftward operation wire 32L, and a rightward operation wire 32R. Although not shown, the distal end portion 32c of each of the operation wires 32 is connected in the inside of the bending portion 7 in such a way that the distal end portion of the upward operation wire 32U is connected to the upper side of the bending portion 7, that the distal end portion of the downward operation wire 32D is connected to the down side of the bending portion 7, that the distal end portion of the leftward operation wire 32L is connected to the left side of the bending portion 7, and that the distal end portion of the rightward operation wire 32R is connected to the right side of the bending portion 7.

Further, the proximal end portion 32b of the each operation wire 32 is fixed to each end of a support plate 23c (as will be described below) which is provided in the pulling operation member 23. The upward operation wire 32U and the downward operation wire 32D are fixed to the support plate 23c at mutually opposing positions. The leftward operation wire 32L and the rightward operation wire 32R are fixed to the support plate 23c at mutually opposing positions, in the direction substantially perpendicular to the direction connecting the positions at which the upward operation wire 32U and the downward operation wire 32D are fixed.

As shown in FIG. 2 and FIG. 3, the pulling operation member 23 is mainly configured by the rod-shaped operation lever 23b, a universal joint 23d which is a bearing provided in the middle of the operation lever 23b, and the support plate 23c provided in the lower end of the operation lever 23b. The operation lever 23b is inserted in a rectangular opening 23f of a frame member 23e provided at the upper end of the frame 14 of the operation portion 5. The upper portion of the operation lever 23b is projected to the outside of the frame 14 from the above described opening 23f. The operation lever 23b is attached to the frame 14 via the universal joint 23d and the frame member 23e.

The pulling operation member 23 is supported to be rotatable forward, backward, and leftward, rightward about the rotation center of the universal joint 23d. The support plate 23c is a plate member having an approximately cross shape, and is attached at the lower end of the operation lever 23b perpendicularly to the operation lever 23b. Operation wire portions 23a are provided at respective ends of the support plate 23c, which ends are directed to the four directions. The proximal end portion 32b of the each operation wire 32 is inserted into the operation wire portion 23a, so as to be attached to the operation lever 23b.

Figure 9:
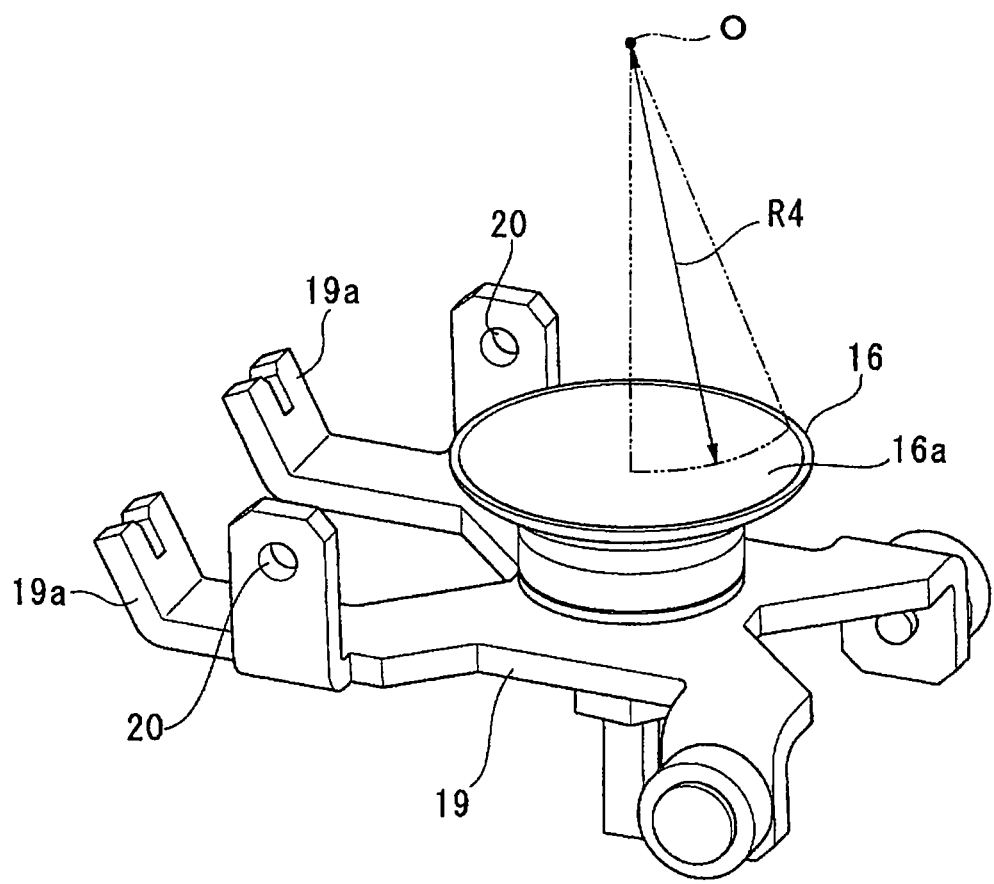
FIG. 9 is a perspective view showing a part of a stopper provided in the locking mechanism.

As shown in FIG. 2 and FIG. 9, for example, a pair of urging members 17 are provided. The urging members 17 are members for pressing a contact surface 16a of a stopper 16 against a spherical surface 15a of a fixed portion 15. In the present embodiment, the urging member 17 is a helical spring configured to be extended in the vertical direction. The lower ends of the urging members 17 are hooked by a pair of hooked portions 14c formed in the frame 14, respectively. The upper ends of the urging members 17 are hooked by a pair of hooked portions 19a formed in a stopper support plate 19, respectively. The hooked portion 19a of the stopper support plate 19 is provided at a position on the front side from each rotation axis 20. That is, there is a positional relationship in which the rotation axis 20 is located between the stopper 16 and the hooked portion 19a.

The hooked portion 19a of the stopper support plate 19 is urged by the above described urging member 17 in the direction so as to be pulled down. The stopper support plate 19 is rotated about the rotation axis 20 by the urging force of the urging member 17, so that the contact surface 16a of the stopper 16 is pressed against the spherical surface 15a of the fixed portion 15. Note that the urging member 17 according to the present invention is not limited to the helical spring, and may be other urging members, such as a plate spring.

A moving mechanism 18 is a mechanism portion for moving the stopper 16, which is brought into close contact with the fixed portion 15, in the direction away from the fixed portion 15 against the urging force of the urging member 17. A known various mechanisms may be used as the moving mechanism 18. For example, it is possible to use a link mechanism which presses down the other end of the stopper support plate 19, specifically a rear side portion of the stopper support plate 19 in the present embodiment, by rotating or vertically moving a locking operation lever 22 provided in the upper rear portion of the operation portion 5.

Further, the operation portion 5 incorporates therein the substrate 21 on which there are mounted electrical components connected to a power switch, a video recording switch, a zoom switch, and an illumination switch which are provided on the side surface of the operation portion 5. The substrate 21 is arranged at a position except the position right below the operation lever 23b, and, specifically, is attached to the side surface outside the frame 14.

Note that the inner diameter of the annular member 36 and the spacer 37 is set to be slightly larger than the outer diameter of the pulley 34. Therefore, it is configured such that the rotation of the pulley 34 is not normally transmitted to the annular member 36.

Further, the above described pulling operation member 23 is configured such that the support plate 23c fixed to the proximal end of the operation lever 23b can be tilted in one of the directions by tilting the operation lever 23b in the direction. Therefore, it is possible, for example, to pull the upward operation wire 32U, and to slacken the downward operation wire 32D by tilting the operation lever 23b in one direction. Further, it is possible, for example, to pull the leftward operation wire 32L, and to slacken the rightward operation wire 32R by tilting the operation lever 23b in the direction different from the one direction by 90 degrees.

Next, the annular member 36 will be described in detail with reference to FIG. 4 to FIG. 7.

Figure 6:
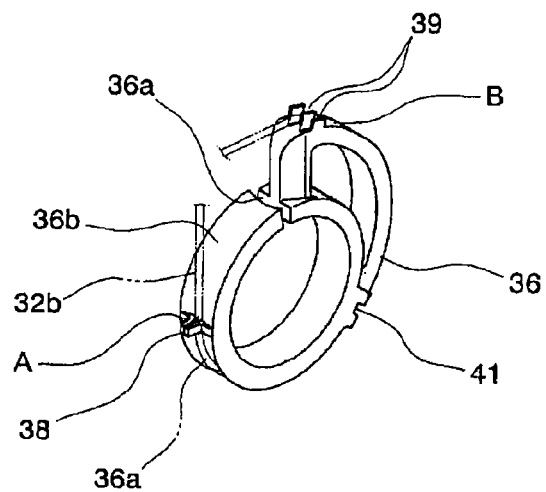
FIG. 6 is a perspective view showing the annular member having a first groove and a second groove which configure the bending mechanism of the endoscope.

As shown in FIG. 4 to FIG. 6, the annular member 36 is set so that the outer diameter thereof is gradually increased. Specifically, the annular member 36 is set so that the outer diameter thereof is gradually increased, from the winding start position A at which the operation wire 32 extended from its proximal end portion 32b connected to the pulling operation member 23 starts to be wound, toward the winding end position B at which the operation wire 32 is extended to the side of the bending portion 7 from the state of being wound.

Further, a first groove 38 and a second groove 39 into which the operation wire 32 can be inserted, are provided around the outer peripheral surface 36b of the annular member 36 so as to be extended in the peripheral direction C. The first groove 38 is formed at the winding start position A, and is located substantially at the center in the width direction X of the annular member 36. Further, the second groove 39 is provided at the winding end position B at two positions which are displaced in the width direction X with respect to the first groove 38 and from the center of the annular member 36 in the width direction X.

Figure 7:
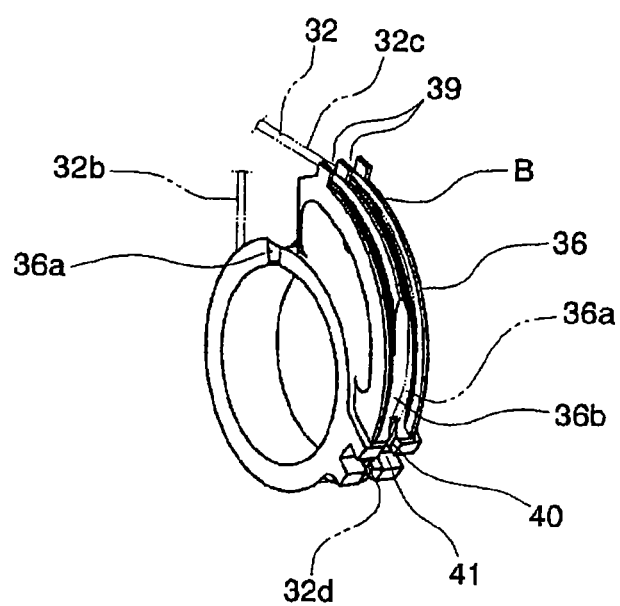
FIG. 7 is a perspective view showing the annular member having a third groove and an engagement recessed portion, in addition to the first groove and the second groove which configure the bending mechanism of the endoscope.

Further, as shown in FIG. 7, on the outer peripheral surface 36b of the annular member 36, an engagement recessed portion 41 together with a third groove 40 into which the wound operation wire 32 can be inserted, are formed between the winding start position A and the winding end position B. Further, a knob-shaped engagement projecting portion 32d corresponding to the engagement recessed portion 41 is formed in the operation wire 32.

As shown in FIG. 4 and FIG. 5, the each operation wire 32 is first inserted in the first groove 38 at the winding start position A on the outer peripheral surface 36b of the annular member 36 corresponding to the each operation wire 32. Subsequently, the each operation wire 32 is inserted in the third groove 40 so that the engagement projecting portion 32d, as a regulating mechanism portion, is fitted into the engagement recessed portion 41. Further, one of the two second grooves 39 is selected, so that the each operation wire 32 is wound by being inserted into the selected second groove 39. Thereby, the wound operation wire 32 is fixed in the width direction X by the first groove 38 and the second groove 39, and wound in the state where its movement in the peripheral direction C is regulated by the regulating mechanism portion configured by the engagement recessed portion 41 of the annular member 36 and the engagement projecting portion 32d of the operation wire 32.

As described above, in the wound operation wire 32, the proximal end portion 32b extended to the pulling operation member 23 crosses with the distal end portion 32c extended to the bending portion 7 in the side view. However, the positions of the first groove 38 and the second groove 39, at which the operation wire 32 is fixed in the width direction X, are displaced from each other in the width direction X. Thus, the operation wire 32 extended to the distal end portion 32c and the operation wire 32 extended to the proximal end portion 32b can be wound in a state of being separated from each other. Note that the portion of the outer peripheral surface 36b of the annular member 36 other than the portions in which the first groove 38, the second groove 39, and the third groove 40 are formed, is formed to have a concave cross section in the width direction X so as to prevent the operation wire 32 from being separated.

Next, the operation of the bending mechanism 31 of the endoscope 2 will be described.

The pulley 34 shown in FIG. 3 is always rotated clockwise in the figure by the drive motor 33. At this time, in the state where the operation lever 23b of the pulling operation member 23 is not tiled in any direction, the each annular member 36 is externally fitted to the pulley 34 with a gap. Thus, the rotation of the pulley 34 is not transmitted to the annular member 36, so that the annular member 36 is in a stationary state. For this reason, the pulling force is not applied to the each operation wire 32, so that the bending portion 7 is also not bent and remains in a linear state.

Next, a case where the bending portion 7 is bent upward will be described.

In this case, the support plate 23c is tilted by tilting the operation lever 23b from the side on which the upward operation wire 32U is fixed, to the side on which the downward operation wire 32D is fixed. Then, regarding the support plate 23c, the position at which the upward operation wire 32U is fixed is moved upward, and the position at which the downward operation wire 32D is fixed is moved downward. Thereby, the proximal end portion 32b of the upward operation wire 32U is pulled, and the proximal end portion 32b of the downward operation wire 32D is slackened.

When the proximal end portion 32b of the upward operation wire 32U is pulled, the annular member 36, around which the operation wire intermediate portion 32a of the upward operation wire 32U is wound, is tightened by the upward operation wire 32U. Thereby, as shown by the two-dot chain line in FIG. 5, the annular member 36 is elastically deformed in a diameter-reducing manner so as to reduce the cut-out 36a, and is brought into close contact with the pulley 34 to which the annular member 36 is externally fitted.

Then, the rotation of the pulley 34 is transmitted to the annular member 36, so that the annular member 36 is rotated clockwise in the figure. Thereby, the operation wire intermediate portion 32a of the wound operation wire 32 is also rotated, so that the distal end portion 32c of the upward operation wire 32U connected to the upper side of the bending portion 7 is pulled and moved to the proximal end side, that is, to the side of the annular member 36, to enable the bending portion 7 to be bent upward. At this time, the distal end portion connected to the bending portion 7 is not directly pulled by the operation of the operation lever 23b, but the operation wire 32 can be pulled by transmitting the rotation of the pulley 34 to the annular member 36 according to the operation of the operation lever 23b. Thus, it is possible to bend the bending portion 7 by a desired bending amount with a small force and by slightly tilting the operation lever 23b.

In particular, in the present embodiment, the outer diameter dimension of the annular member 36 at the winding end position B is set larger than the outer diameter dimension of the annular member 36 at the winding start position A, so that the moving amount of the operation lever 23b can be effectively reduced.

Further, the engagement projecting portion 32d is engaged with the engagement recessed portion 41, so as to regulate the operation wire 32 having the operation wire intermediate portion 32a wound around the annular member 36, from being moved with respect to the annular member in the peripheral direction C. This prevents the position of the operation wire 32 from being shifted on the outer peripheral surface 36b of the annular member 36 in the peripheral direction C. Thereby, the rotation of the pulley 34 can be surely transmitted to the operation wire 32, so as to bend the bending portion 7.

As the bending amount of the bending portion 7 is increased, the necessary pulling force of the operation wire 32 is increased. That is, when the pulling force of the operation wire 32 reaches a fixed amount, the annular member 36 is tightened by the operation wire 32 which is wound around the annular member 36. However, in this state, the annular member 36 and the pulley 34 start to slip therebetween, and the rotation of the annular member 36 is stopped in a predetermined position. For this reason, the bending portion 7 can be bent by a predetermined amount according to the operation of the operation lever 23b without being excessively bent, and the bending state can be kept in a stable state.

Note that in the above description, the downward operation wire 32D facing the upward operation wire 32U is slackened, and hence the operation for bending the bending portion 7 upward by the upward operation wire 32U is not obstructed.

Further, the each operation wire 32 is wound around the each separate annular member 36 which is paired with the each operation wire 32, and hence the rotation of the pulley 34 can be independently transmitted to the each operation wire 32. In particular, by providing the spacer 37 between the adjacent annular members 36, it is possible to prevent that the annular members 36 interfere with each other so as to be rotated together. Thereby, the annular members 36 can be more surely rotated independently from each other, so as to make the bending portion 7 bent in the desired direction.

As shown in FIG. 4 and FIG. 5, when the operation wire 32 is pulled to bend the bending portion 7, the proximal end portion 32b connected to the support plate 23c is pulled and moved to the side of the pulling operation member 23, while the distal end portion 32c which is extended so as to cross the proximal end portion 32b and is connected to the bending portion 7, is pulled and moved to the side of the annular member 36. However, in the annular member 36, the positions of the first groove 38 and the second groove 39 are shifted from each other in the width direction X, so that the distal end portion 32c and the proximal end portion 32b of the operation wire 32 are held in the separated state and thereby are prevented from being rubbed with each other. For this reason, when the operation wire 32 is pulled by operating the operation lever 23b, it is possible to prevent that the operation wires 32 are rubbed with each other to thereby obstruct the operation for reducing the diameter of the annular member 36. Thus, the bending portion 7 can be efficiently bent.

Further, there is no possibility that the operation wires 32 are damaged and disconnected by being rubbed with each other. Thus, it is possible to improve the durability of the operation wires 32.

Further, in the annular member 36, the second grooves 39 are provided at two places different from the position of the first groove 38 in the width direction X. Thereby, one of the two second grooves 39 for the each operation wire 32 can be selected on the basis of the relative positional relationship between the distal end portion 32c and the proximal end portion 32b of the operation wire 32, so as to enable the each operation wire 32 to be fixed at the position in the width direction X, which position is most suitable for preventing the each operation wire 32 from being rubbed with the other operation wire.

Further, a position most suitable for the condition of the each operation wire 32 can be selected in the same annular member 36. This eliminates the need to change the shape of the annular member 36 in dependence upon the condition of the operation wire 32, and hence the manufacturing cost can be reduced.

Further, as shown in FIG. 2 and FIG. 3, it is only necessary to return the tilted operation lever 23b to the original state, in order to return the bending portion 7 in the bent state to the linear state. By operating in this way, the upward operation wire 32U in the state of being pulled is slackened, and thereby the operation wire intermediate portion 32a of the upward operation wire 32U is set to the slackened state from the state of tightening the annular member 36. Thereby, the diameter of the annular member 36 is elastically increased, so that the rotation of the pulley 34 is prevented from being transmitted. As a result, the bending portion 7 is returned to the linear state. At this time, the operation wire 32 is set in the state of being slackened around the outer peripheral surface 36b of the annular member 36. However, since the operation wire 32 is regulated by the engagement recessed portion 41 of the annular member 36 and the engagement projecting portion 32d of the operation wire 32, it is prevented that the operation wire 32 is moved with respect to the annular member 36 and that the position of the operation wire 32 is shifted in the width direction X on the annular member 36. Thus, the operation wires 32 can be more surely prevented from being rubbed with each other.

Note that in the present embodiment, it is assumed that four paired sets of the operation wire 32 and the annular member 36 are provided. However, the number of the paired sets of the operation wire 32 and the annular member 36 is not limited to four. The bending portion 7 can be bent to a predetermined direction corresponding to the number of the operation wires 32 by providing at least the one paired set.

Further, it is assumed that the second groove 39 is provided at two places in the annular member 36. However, the configuration of the second groove 39 is not limited thereto. It is possible to prevent the operation wires 32 from being rubbed with each other by such a way that the second groove is provided at least at one place which is shifted in the width direction X from the first groove 38. Further, when the second grooves 39 are provided at three or more places, the selectable places in the width direction X are increased, so that a more suitable position can be selected.

Further, it is possible to expect the same effect by providing a plurality of the first grooves 38 in the width direction X instead of the second groove 39.

Note that in the present embodiment, it is assumed that the endoscope 2 is used by being attached to the apparatus main body 3 having the monitor 9 or the battery, but the present invention is not limited thereto. The endoscope 2 may also be specified such that the monitor and the battery are directly provided in the endoscope 2.

Figure 8:
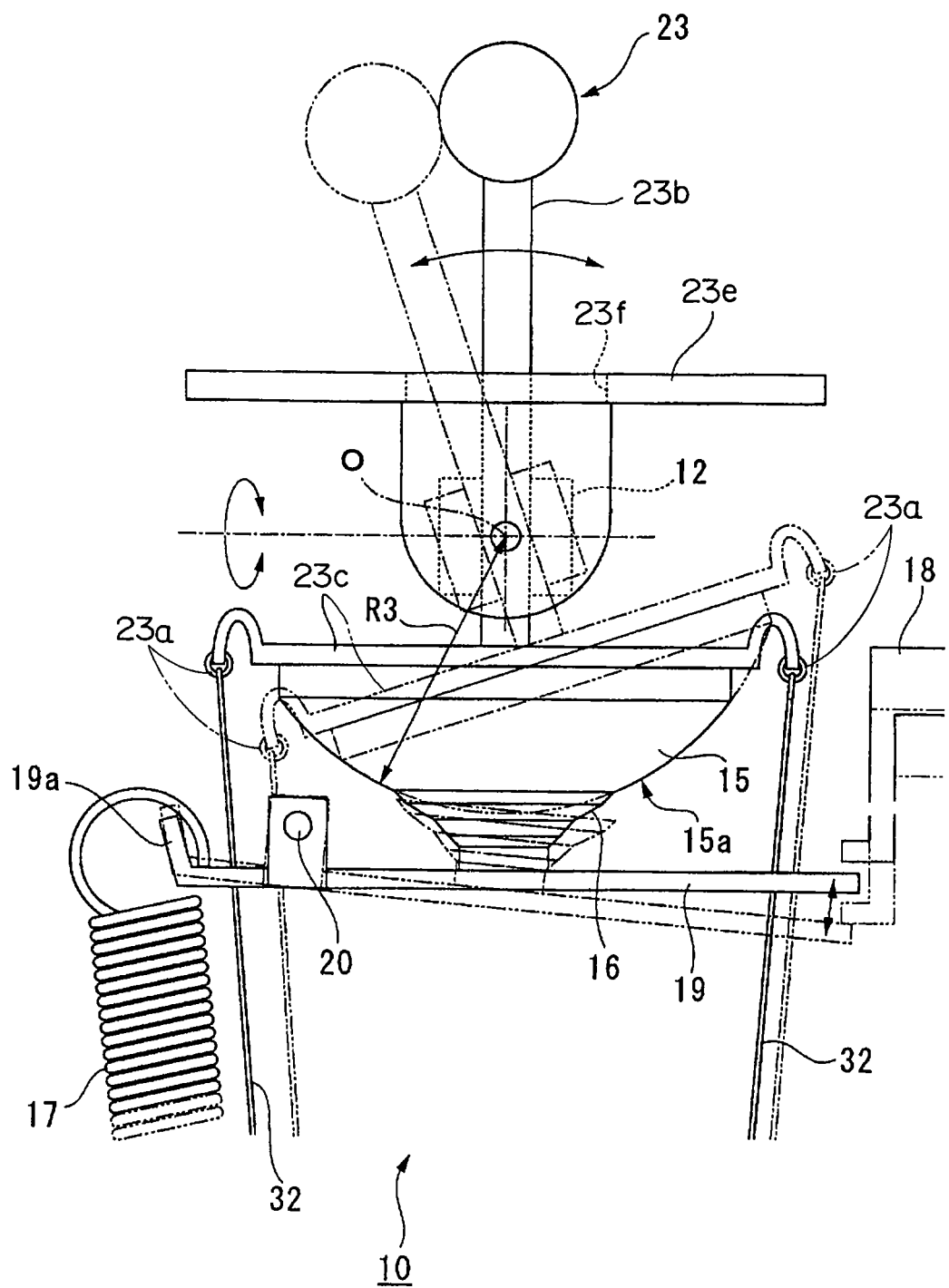
FIG. 8 is a side view showing a part of a locking mechanism provided in the operation portion of the endoscope.

As shown in FIG. 2 and FIG. 8, the locking mechanism 11 is a mechanism configured to bring the stopper 16 into close contact with the spherical surface 15a of the fixed portion 15 provided on the side of the pulling operation member 23, so as to thereby regulate the rotatable movement of the pulling operation member 23. The locking mechanism 11 is substantially configured by including the fixed portion 15 provided on the side of the pulling operation member 23, the stopper 16 which is brought into close contact with the spherical surface 15a of the fixed portion 15, the urging members 17 which urge the stopper 16, and the moving mechanism 18 which moves the stopper 16.

The fixed portion 15 is a circular member, on one side of which the spherical surface 15a is formed. The fixed portion 15 is provided at the lower end of the pulling operation member 23 in the state where the spherical surface 15a is downwardly directed. The fixed portion 15 is attached to the lower surface of the support plate 23c, so as to be integrated with the pulling operation member 23. The spherical surface 15a of the fixed portion 15 is a spherical surface formed with a predetermined radius R3 about the rotation center point O of the universal joint 12.

As shown in FIG. 2, FIG. 8, and FIG. 9, the stopper 16 is a member to be brought into close contact with the fixed portion 15. The side of the contact surface 16a, which is brought into contact with the fixed portion 15, is formed into a spread suction disk shape, and is formed by a member of an elastically deformable material, such as rubber. That is, the stopper 16 is a cup-shaped member spread in a conical shape, and the contact surface 16a which is the end surface on the spread side of the member, is formed into a spherically recessed shape.

Further, the contact surface 16a of the stopper 16 is formed as a spherical surface with a curvature slightly larger than that of the spherical surface 15a of the fixed portion 15. Specifically, the spherical radius R4 of the spherical contact surface 16a of the stopper 16 is smaller than the spherical radius R3 of the spherical surface 15a of the fixed portion 15. In other words, the curvature (1/R4) of the contact surface 16a of the stopper 16 is larger than the curvature (1/R3) of the spherical surface 15a of the fixed portion 15.

Further, the stopper 16 is fixed in the state of being mounted on the upper surface of the plate-shaped stopper support plate 19. The stopper support plate 19 is attached to the frame 14 so as to be rotatable in the vertical direction. Specifically, shaft portions arranged in holes denoted by reference numerals 20 and 20 as shown in FIG. 9 serve as the rotation shafts, so that the stopper support plate 19 is attached to the frame 14 in a vertically rotatable manner.

Note that the stopper 16 is arranged substantially at the center position of the stopper support plate 19, and the rotation shafts 20 and 20 of the stopper support plate 19 are provided at positions near the one side of the stopper support plate 19, that is, at positions near the front in the present embodiment.

Further, when the bent state of the bending portion 7 is to be held as described above, the bent state of the bending portion 7 is held by operating the locking operation lever 22 of the locking mechanism 11 and regulating the movement of the pulling operation member 23. In an ordinary operation, that is, when the lock is released, the other end portion of the stopper support plate 19 is pressed down by the moving mechanism 18, so that the stopper 16 is in a state of being separated from the fixed portion 15. In this state, the movement of the pulling operation member 23 is not regulated, so that the bending portion 7 can be bent by the above described operation of the operation lever 23b.

On the other hand, the locking operation lever 22 is operated, so as to release the moving mechanism 18 pressing down the other end portion of the stopper support plate 19, and thereby the bending portion 7 is locked. Specifically, when the moving mechanism 18 is released, and when the downward pressing by the other end portion of the stopper support plate 19 is removed, the one end portion of the stopper support plate 19 is pulled down by the urging force of the urging members 17 and 17, so that the stopper support plate 19 is rotated. Thereby, the contact surface 16a of the stopper 16 is pressed against the spherical surface 15a of the fixed portion 15 so as to be brought into close contact with the spherical surface 15a. In this way, in the state where the stopper 16 and the fixed portion 15 are brought into close contact with each other, the movement of the pulling operation member 23 is regulated by a frictional force caused between the contact surface 16a of the stopper 16 and the spherical surface 15a of the fixed portion 15, so that the bending portion 7 is fixed in the bent state.

According to the endoscope 2 configured as described above, the bending portion 7 of the endoscope insertion portion 4 can be suitably bent, and hence the observed position can be accurately captured. Further, since the bending portion 7 can be locked by the locking mechanism 11, the observation can be performed in the state where the bending portion 7 is held in the bent state.

Figure 10:
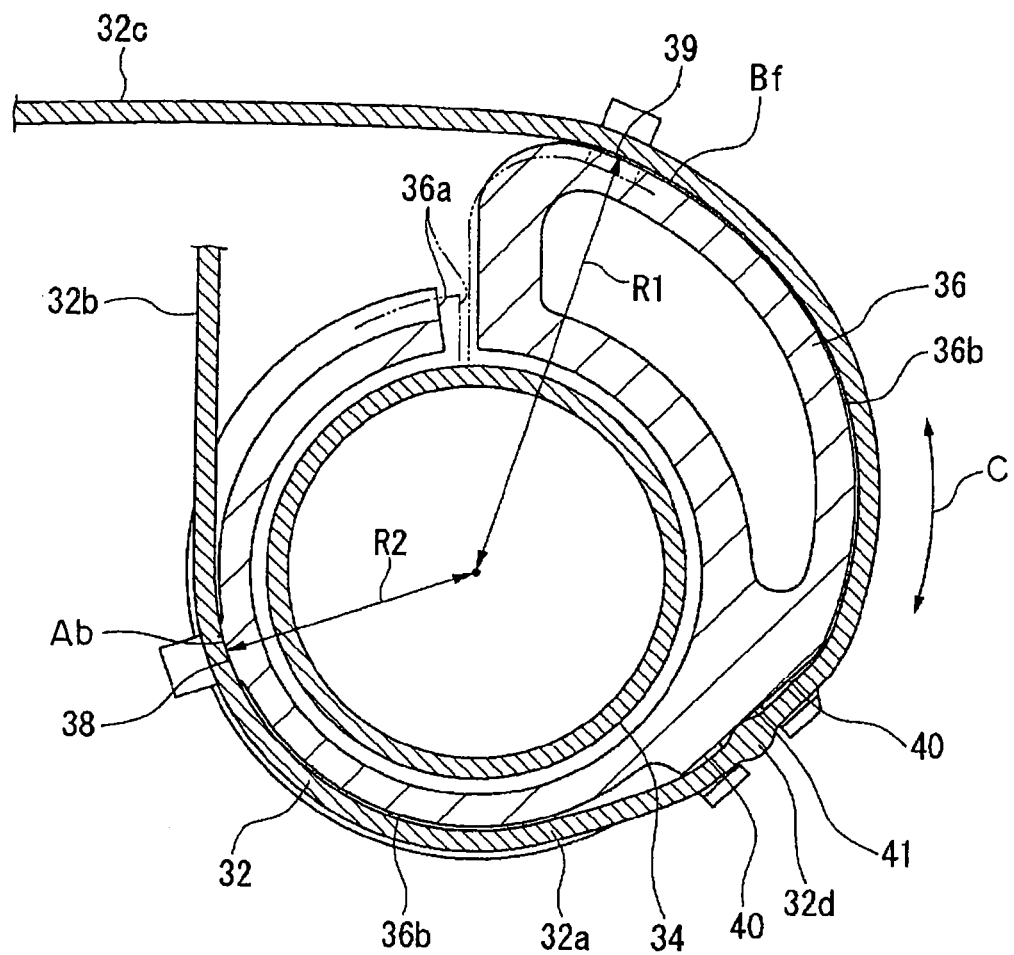
FIG. 10 is a sectional view showing the pulley and the annular member which are provided in the bending mechanism of the endoscope.

As shown in FIG. 10, the annular member 36 has a shape in which the outer diameter R1 at the distal end side position Bf is larger than the outer diameter R2 at the proximal end side position Ab. Specifically, the annular member 36 has a shape like a spiral shellfish, in which shape the outer diameter is gradually increased from the proximal end side position Ab to the distal end side position Bf.

Note that the above described proximal end side position Ab is the position where the proximal end side portion of the operation wire intermediate portion 32a wound around the annular member 36 is wound, and is the position where the operation wire 32 extended from the proximal end side is wound around the annular member 36.

Further, the distal end side position Bf is the position where the distal end side portion of the operation wire intermediate portion 32a wound around the annular member 36 is wound, and is the position where the operation wire 32 extended from the distal end side is wound around the annular member 36.

The outer diameter R1 at the distal end side position Bf of the annular member 36 is larger than the outer diameter R2 at the proximal end side position Ab of the annular member 36. Thus, according to the principles of lever, the pulling amount of the distal end side pulling the bending portion 7 is larger than the pulling amount of the proximal end side pulled by the pulling operation member 23.

In this way, the distal end side of the operation wire 32 can be efficiently pulled by the pulling operation member 23, and hence the bending portion 7 provided at the distal end of the endoscope insertion portion 4 can be significantly bent.

On the other hand, as shown in FIG. 8 and FIG. 9, when the outer diameter R1 at the distal end side position Bf of the annular member 36 is larger than the outer diameter R2 at the proximal end side position Ab of the annular member 36, as described above, the burden applied to the stopper 16 which is in the state of being locked by the locking mechanism 11 as shown in FIG. 2, becomes large. This is because according to principles of lever, a tensile force larger than that on the side of the distal end portion 32c is applied to the proximal end portion 32b of the operation wire 32 wound around the annular member 36 in which the outer diameter R1 at the distal end side position Bf is larger than the outer diameter R2 at the proximal end side position Ab, and thereby the force to return the tilted pulling operation member 23 to the original state becomes large.

In this way, the movement of the pulling operation member 23 may not be surely regulated when the burden applied to the stopper 16 becomes large. However, in the endoscope 2 having the above described configuration, the stopper 16 is formed to have suction disk shape, and hence the stopper 16 and the fixed portion 15 are easily brought into close contact with each other. Thereby, even when the load applied to the stopper 16 is large, the movement of the pulling operation member 23 is surely regulated.

That is, the suction disk shaped stopper 16 has a large contact area, and its edge portion is easily deformed, so that the whole contact surface 16a of the stopper 16 is easily brought into close contact with the spherical surface 15a of the fixed portion 15. Thereby, the frictional force caused between the fixed portion 15 and the stopper 16 is increased, so that the movement of the pulling operation member 23 can be surely prevented. Therefore, as described above, even when the outer diameter R1 at the distal end side position Bf of the annular member 36 is larger than the outer diameter R2 at the proximal end side position Ab of the annular member 36, and even when the load applied to the stopper 16 is large, the bending portion 7 is surely held in a state of being bent.

Further, according to the endoscope 2 having the above described configuration, the spherical radius R4 (as shown in FIG. 9) of the spherically shaped contact surface 16a of the stopper 16 is slightly smaller than the spherical radius R3 (as shown in FIG. 8) of the spherical surface 15a of the fixed portion 15. Thereby, the contact surface 16a of the stopper 16 can be more easily brought into close contact with the spherical surface 15a of the fixed portion 15, so that the bending portion 7 can be more surely held in the bent state.

Further, the locking mechanism 11 according to the above described embodiment includes the urging member 17 which urges the stopper 16 to the side of the spherical surface 15a of the fixed portion 15, and the moving mechanism 18 which moves the stopper 16 in close contact with the spherical surface 15a of the fixed portion 15, in the direction away from the spherical surface 15a. However, the locking mechanism according to the present invention may include a moving mechanism which presses the stopper against the spherical surface of the fixed portion, and an urging member which urges the stopper in the direction away from the spherical surface of the fixed portion.

Further, in the above described embodiment as shown in FIG. 2, the stopper 16 is a member having a suction disk shape which is spread on the side of the contact surface 16a in contact with the fixed portion 15, that is, a member which has a conically spread shape with the contact surface 16a spherically recessed. However, according to the present invention, it is possible to use a stopper having a shape other than the above described shape. For example, a stopper formed to have a pyramid-like spread shape may be used, or a stopper formed not to have a recessed spherical surface shape but to have a recessed curved surface shape may also be used. Further, a stopper made of a material excellent in elastic property may also be formed to have a flat contact surface.

Another configuration of the annular member 36 as the rotating body will be described in detail with reference to FIG. 11 to FIG. 16.

First, as shown in FIG. 11 to FIG. 14, similarly to the annular member 36, an annular member 136 according to the present embodiment is set so that the outer diameter of the annular member 136 is gradually increased from the winding start position A where the operation wire 32 connected to the pulling operation member 23 starts to be wound, to the winding end position B where the operation wire 32 is wound and extended to the side of the bending portion 7.

Figure 12:
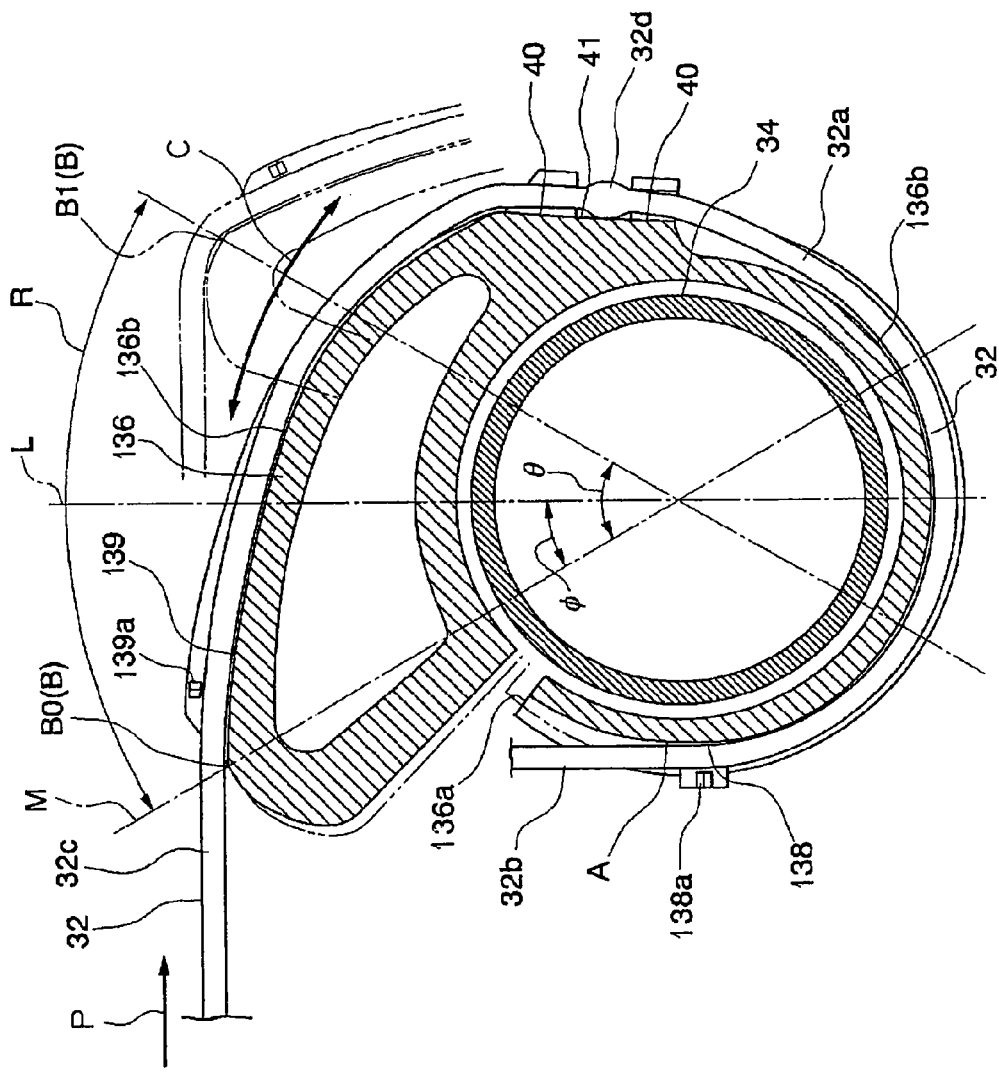
FIG. 12 is a sectional view explaining the pulley and an annular member having another configuration which are provided in the bending mechanism of the endoscope.

As shown in FIG. 12, in the initial state corresponding to the pulling operation member 23, the annular member 136 is externally fitted to the pulley 34 in such a manner that the winding end position B of the operation wire 32 is located at the initial position B0 on the side of the bending portion 7 with respect to a reference line L passing through the center of the shaft body 34a. Here, the reference line L is a straight line substantially orthogonal to the direction in which the distal end portion 32c of the operation wire 32 is arranged, that is, substantially orthogonal to the pulling direction P.

On the other hand, as will be described below, the proximal end portion 32b of the operation wire 32 is pulled by the pulling operation member 23, and thereby the annular member 136 is rotated by the rotational angle corresponding to the pulling amount of the proximal end side of the operation wire 32. Then, when the proximal end portion 32b of the operation wire 32 is pulled by the proximal end side maximum pulling amount by the pulling operation member 23, the rotational angle of the annular member 136 becomes the maximum rotation angle θ, so that the winding end position B of the operation wire 32 is retreated from the initial position B0 to the maximum pulling position B1.

Here, in the present embodiment, when the operation wire 32 is pulled by the proximal end side pulling amount, the maximum rotation angle θ is set to become approximately 90 degree. Further, the initial position B0 is located on the side of the bending portion 7 from the reference line L as described above, while the maximum pulling position B1 of the winding end position B is set so as to be located on the opposite side with respect to the reference line L.

Further, in the case of the present embodiment, the angle ϕ between the line M connecting the initial position B0 to the center of shaft body 34a and the reference line L is set to be substantially half the amount of the maximum rotation angle θ of the annular member 136. That is, the range R of the rotational movement of the winding end position B, which is caused by the proximal end portion 32b of the operation wire 32 being pulled by the pulling operation member 23, is set to be substantially equally divided by the reference line L. Specifically, it is configured such that the winding end position B can be rotated by 45 degrees from the reference line L to the side of the bending portion 7, and can be rotated by 45 degrees from the reference line L to the opposite side.

Further, similarly to the first groove 38 and the second groove 39, a first groove 138 and a second groove 139 into which the operation wire 32 can be inserted, are extended on the outer peripheral surface 136b of the annular member 136 in the peripheral direction C.

Figure 15:
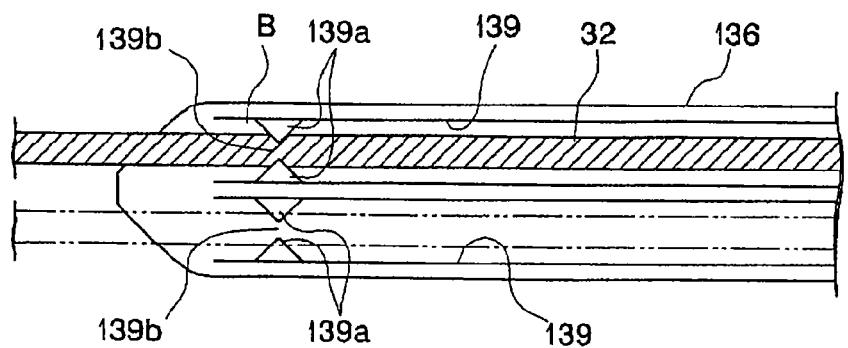
FIG. 15 is a detail view of the first groove of the annular member.

Here, as shown in FIG. 12 and FIG. 15, a pair of projecting portions 138a and 138a are provided so as to project from the both side surfaces of the first groove 138 on the outside in the radial direction of the annular member 136. The pair of projecting portions 138a are set to secure a space for enabling the operation wire 32 to be received in the inside in the radial direction of the first groove 138, and are set to make the gap 138b between the projecting portions 138a slightly smaller than the outer diameter of the operation wire 32.

For this reason, it is configured such that the operation wire 32 can be received in the first groove 138 by elastically deforming the pair of projecting portions 138a, and that in the received state, the operation wire is regulated by the pair of projecting portions 138a from being moved from the first groove 138 to the outside in the radial direction. That is, a first regulating mechanism portion is configured by the pair of projecting portions 138a.

Figure 16:
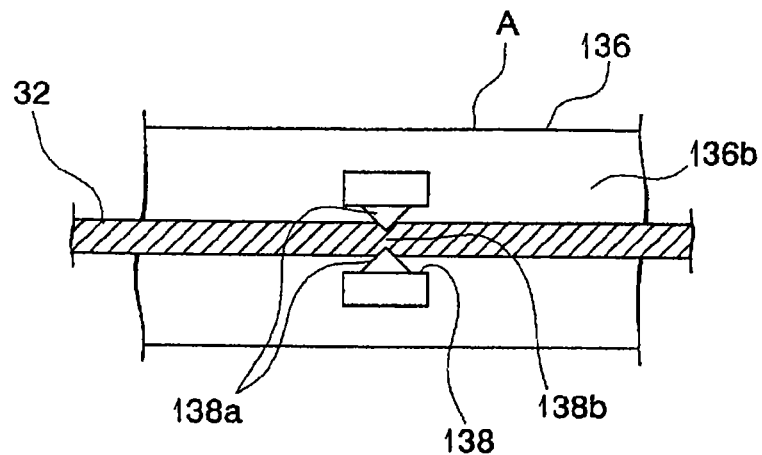
FIG. 16 is a detail view of the second groove of the annular member.

Similarly as shown in FIG. 12 and FIG. 16, a pair of projecting portions 139a and 139a are provided in each of the second groove 139 so as to project from the both side surfaces of the second groove 139 on the outside in the radial direction of the annular member 136. Thus, a first regulating mechanism portion is configured which regulates, by the pair of projecting portions 139a, the operation wire 32 from being moved from the second groove 139 to the outside in the radial direction.

Note that in the above description, it is assumed that the projecting portions 138a and 139a are respectively formed in the first groove 138 and the second groove 139, on the outside in the radial direction of the annular member 136. However, the projecting portions 138a and 139a may also be formed over the whole radial direction, so as to sandwich the operation wire 32 in the first groove 138 and the second groove 139.

Figure 14:
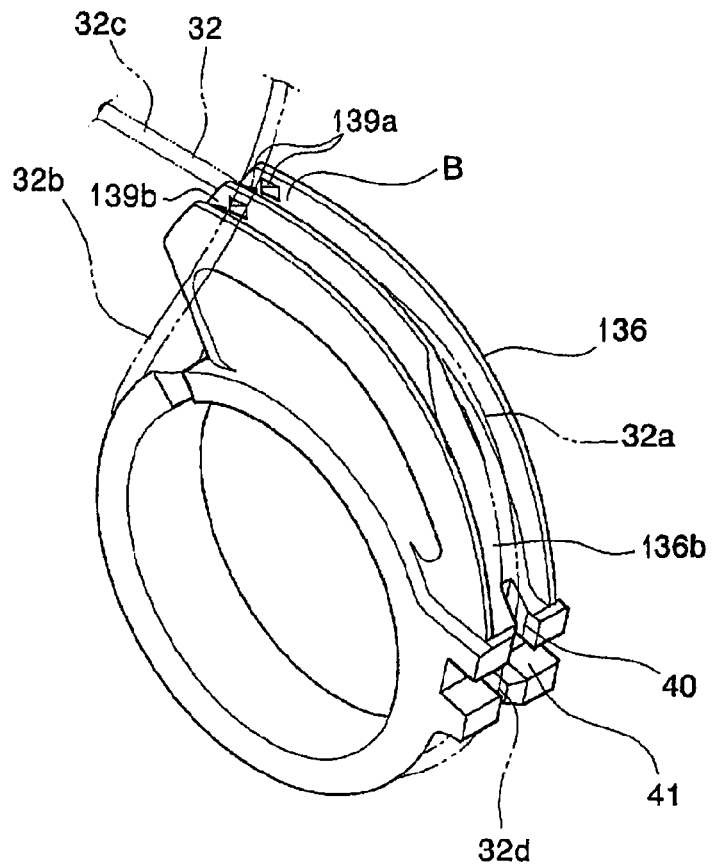
FIG. 14 is a perspective view in which the annular member of FIG. 12 is viewed from the rear side.

Further, as shown in FIG. 12 and FIG. 14, the engagement recessed portion 41 is formed together with the third groove 40 into which the wound operation wire 32 can be inserted, between the winding start position A and the winding end position B on the outer peripheral surface 136b of the annular member 136. Further, the knob-shaped engagement projecting portion 32d is formed in the operation wire 32 so as to correspond to the engagement recessed portion 41.

Figure 13:
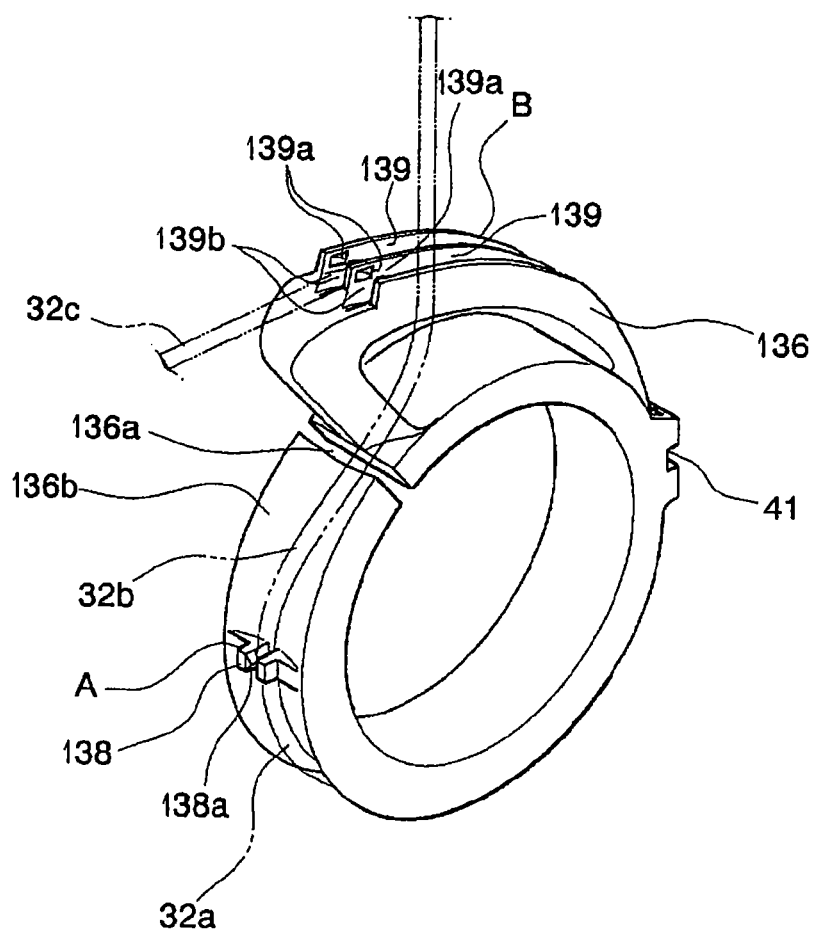
FIG. 13 is a perspective view in which the annular member of FIG. 12 is viewed from the front side.

Then, as shown in FIG. 12 and FIG. 13, the each operation wire 32 is inserted into the first groove 138 at the winding start position A on the outer peripheral surface 136b of the corresponding annular member 136, and is inserted into the third groove 40. Also, the engagement projecting portion 32d as the second regulating mechanism portion is fitted in the engagement recessed portion 41. Further, one of the two second grooves 139 is selected, and the each operation wire 32 is wound around the annular member 136 by being inserted into the selected second grooves 139.

For this reason, the wound operation wire 32 is fixed in the width direction X by the first groove 138 and the second groove 139. The radial movement of the wound operation wire 32 is regulated by the projecting portions 138a and 139a which are the first regulating mechanism portions. Further, the movement in the peripheral direction C of the wound operation wire 32 is regulated by the second regulating mechanism portion which is configured by the engagement recessed portion 41 of the annular member 136 and the engagement projecting portion 32d of the operation wire 32.

At this time, as described above, in the wound operation wire 32, the proximal end portion 32b extended to the pulling operation member 23 and the distal end portion 32c extended to the bending portion 7 cross with each other in the side view. However, the first groove 138 and the second groove 139, which fix the operation wire 32 in the width direction X, are provided so as to be positionally shifted in the width direction X from each other. As a result, the distal end portion 32c and the proximal end portion 32b of the operation wire 32 can be wound in the state of being separated from each other in the width direction X.

Note that the portion of the outer peripheral surface 136b of the annular member 136 other than the portion in which the first groove 138, the second groove 139, and the third groove 40 are formed, is formed to have a recessed cross section in the width direction X, so as to prevent the operation wire 32 from being disengaged.

Next, the operation of the bending mechanism 31 of the endoscope 2 will be described.

The pulley 34 shown in FIG. 3 is always rotated clockwise in the figure by the drive motor 33. At this time, in the initial state in which the operation lever 23b of the pulling operation member 23 is not tilted in any direction, the each annular member 136 is externally fitted to the pulley 34 with a gap as shown in FIG. 12. Thus, the rotation of the pulley 34 is not transmitted to the annular member 136, and hence the annular member 136 is in the stationary state. At this time, the position of the winding end position B of the operation wire 32 is set at the initial position B0. No pulling force is applied to the distal end portion 32c of the each operation wire 32, and the bending portion 7 is not bent, so as to remain in the linear state.

Next, a case where the bending portion 7 is bent upward will be described.

In this case, the operation lever 23b is tilted from the side on which the upward operation wire 32U is fixed, to the side on which the downward operation wire 32D is fixed, so as to tilt the support plate 23c. Thereby, the position of the support plate 23c at which the upward operation wire 32U is fixed is moved upward, while the position of the support plate 23c at which the downward operation wire 32D is fixed is moved downward. Thereby, the proximal end portion 32b of the upward operation wire 32U is pulled, and the proximal end portion 32b of the downward operation wire 32D is slackened.

When the proximal end portion 32b of the upward operation wire 32U is pulled, the annular member 136 around which the winding operation wire intermediate portion 32a of the upward operation wire 32U is wound, is tightened by the upward operation wire 32U. Thereby, as shown in FIG. 12, the annular member 136 is elastically deformed in a diameter-reducing manner so as to reduce a cut-out 136a, and hence is brought into close contact with the pulley 34 to which the annular member 136 is externally fitted. Thereby, the rotation of the pulley 34 is transmitted to the annular member 136, so that the annular member 136 is rotated clockwise in the figure together with the pulley 34. As a result, the wound operation wire intermediate portion 32a of the operation wire 32 is also rotated, so that the winding end position B is retreated to the proximal end portion side. Then, the distal end portion 32c of the upward operation wire 32U connected to the upper side of the bending portion 7 is pulled and moved to the side of the proximal end portion, that is, to the side of the annular member 136, and thereby, the bending portion 7 is bent upward.

Then, as the bending amount of the bending portion 7 is increased, the amount of force required for pulling the operation wire 32 is increased. On the other hand, the proximal end portion 32b of the operation wire 32 starts to be slackened by the rotation of the annular member 136. For this reason, when the bending amount of the bending portion 7 reaches a fixed level in the state where the tilting angle of the operation lever 23b of the pulling operation member 23 is kept constant, the distal end portion 32c of the operation wire 32 is restrained by the bending portion 7, and the force for tightening the annular member 136 by the operation wire 32 is reduced.

Thereby, the annular member 136 and the pulley 34 start to slip, so that the rotation of the annular member 136 is stopped at the position corresponding to the proximal end side pulling amount of the proximal end portion 32b of the operation wire 32 pulled by the pulling operation member 23. For this reason, the bending portion 7 can be bent by the predetermined bending amount corresponding to the operation of the operation lever 23b, and can also be prevented from being excessively bent. Also, the bending state of the bending portion 7 can be kept in the stationary state.

Further, when the operation lever 23b of the pulling operation member 23 is tilted by the maximum angle, the winding end position B of the operation wire 32 is moved from the initial position B0 to the maximum pulling position B1, so that the bending amount of the bending portion 7 reaches the maximum value in the direction corresponding to the tilting direction of the operation lever 23b.

At this time, the distal end portion 32c of the operation wire 32 connected to the bending portion 7 is not directly pulled by the operation of the operation lever 23b, but is pulled by transmitting the rotational drive force of the pulley 34 in correspondence with the operation of the operation lever 23b. Thus, the bending portion 7 can be bent by a desired bending amount by tilting the operation lever 23b with a small force by a small moving amount.

Further, in the annular member 136, the winding end position B of the operation wire 32 is rotated and moved from the initial position B0 to the maximum pulling position B1 beyond the reference line L substantially perpendicular to the pulling direction P of the distal end portion 32c of the operation wire 32. For this reason, it is possible to increase the component in the pulling direction P of the moving amount based on the rotational movement of the winding end position B of the operation wire 32, so that the distal end portion 32c of the operation wire 32 can be pulled and moved by efficiently converting the moving amount of the winding end position B into the pulling amount of the distal end portion 32c of the operation wire 32.

In particular, in the present embodiment, the rotational movement range R of the winding end position B is set to be substantially equally divided by the reference line L perpendicular to the pulling direction P. Thus, the component in the pulling direction P of the moving amount of the winding end position B can be maximized, so that the distal end portion 32c of the operation wire 32 can be more efficiently pulled and moved.

Further, in the present embodiment, the outer diameter of the annular member 136 is set to be larger at the winding end position B than at the winding start position A. Thus, the moving amount of the winding end position B can be increased as compared with the pulling amount of the proximal end portion 32b of the operation wire 32 pulled by the operation lever 23b, so that the distal end portion 32c can be more efficiently pulled and moved.

Further, the operation wire 32 having the operation wire intermediate portion 32a wound around the annular member 136, and the annular member 136 are regulated from being moved to each other in the peripheral direction C by the engagement projecting portion 32d being engaged with the engagement recessed portion 41. Thereby, the operation wire 32 is prevented from being positionally shifted in the peripheral direction C on the outer peripheral surface 36b of the annular member 136. For this reason, the bending portion 7 can be bent by surely transmitting the rotation of the pulley 34 to the operation wire 32.

Note that also in the present embodiment, the downward operation wire 32D facing the upward operation wire 32U is slackened, and hence the operation for bending the bending portion 7 upward by the upward operation wire 32U is not obstructed by the downward operation wire 32D. At this time, the projecting portions 138a and 139a serving as the first regulating mechanism portion are provided to each of the first groove 138 and the second groove 139, so that the slackened downward operation wire 32D can be prevented from being moved to the outside in the radial direction and from being disengaged.

Further, the each operation wire 32 is wound around the separate annular member 136 which is paired with the each operation wire 32, so that the each operation wire 32 can be pulled by independently transmitting the rotation of the pulley 34 to the each operation wire 32. In particular, the spacer 37 is provided between the adjacent annular members 136, so that the annular members 136 are prevented from interfering with each other and from being rotated together. Thereby, the annular members 136 can be more surely independently rotated to bend the bending portion 7 in the desired direction.

Figure 11:
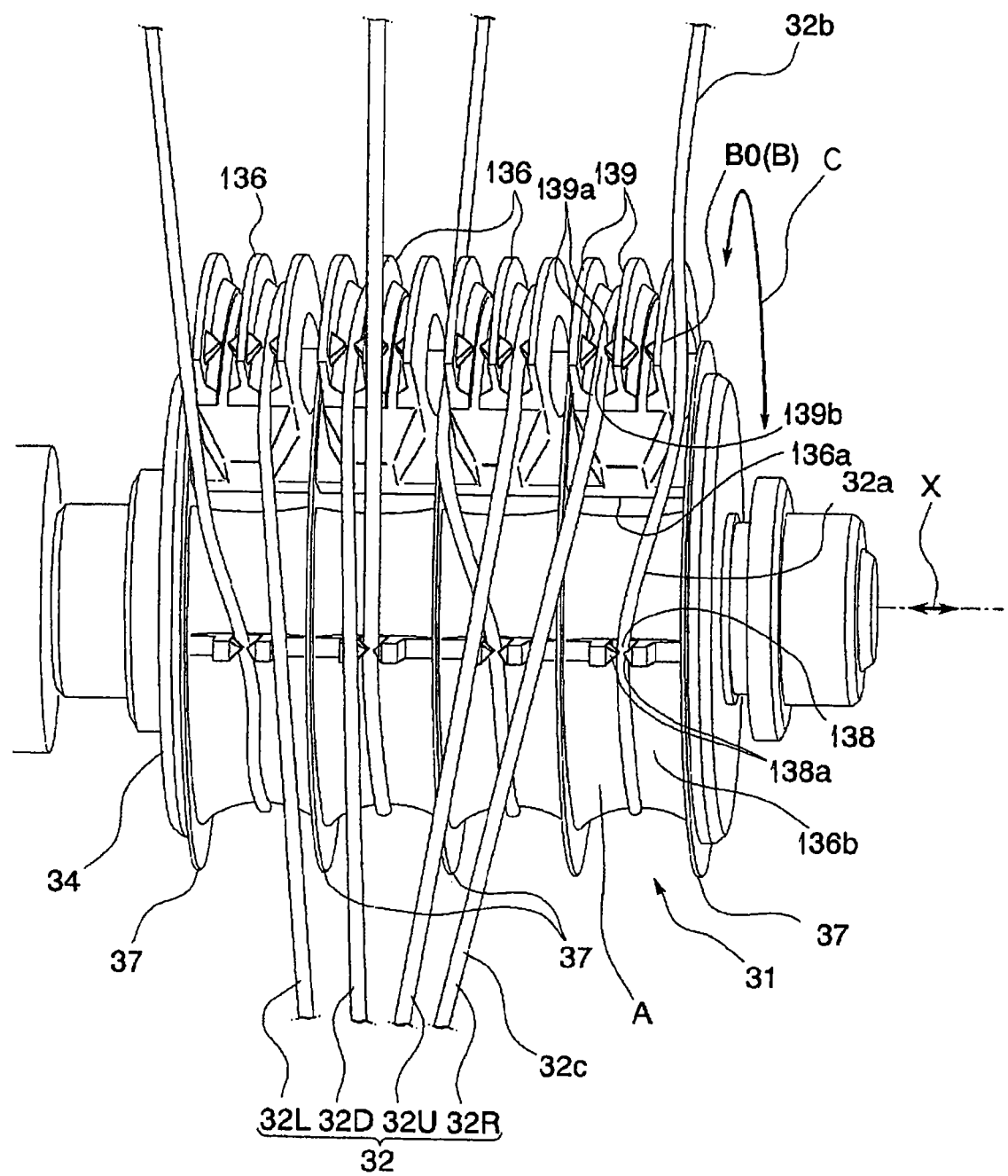
FIG. 11 is a perspective view showing a part of another configuration of the bending mechanism provided in the operation portion of the endoscope.

Here, when the bending portion 7 is bent by pulling the operation wire 32 as shown in FIG. 11 and FIG. 12, the proximal end portion 32b connected to the support plate 23c is pulled and moved to the side of the pulling operation member 23, while the distal end portion 32c which is extended so as to cross with the proximal end portion 32b and is connected to the bending portion 7, is pulled and moved to the side of the annular member 136. However, in the annular member 136, the first groove 138 and the second groove 139 are positionally shifted from each other in the width direction X. Thereby, the distal end portion 32c and the proximal end portion 32b of the operation wire 32 can be maintained in the separated state, so as to be prevented from being rubbed with each other. For this reason, it is prevented that when the operation wires 32 is pulled by the operation of the operation lever 23b, the operation wires 32 are rubbed with each other, so as to thereby obstruct the operation to reduce the diameter of the annular member 136. As a result, the bending portion 7 can be efficiently bent.

Further, there is no possibility that the operation wires 32 are damaged and disconnected by being rubbed with each other. Thus, the durability of the operation wire 32 can be improved.

Further, in the annular member 136, the second groove 139 is provided at two positions which are different in the width direction X from the position of the first groove 138. Thereby, the each operation wire 32 can be fixed in the width direction X by such a way that one of the second grooves 139, which is most suitable to prevent the operation wires 32 from being rubbed with each other, is selected for the each operation wire 32, on the basis of the relative positional relationship between the distal end portion 32c and the proximal end portion 32b of the operation wire 32.

Further, it is possible to select the position most suitable for the condition of the each operation wire 32 by using the same annular member 136. Thus, the shape of the annular member 136 need not be changed according to the condition of the operation wire 32, and thereby the manufacturing cost can be reduced.

Further, the tilted operation lever 23b is only returned to the original state in order to return the bent bending portion 7 to the linear state. When such operation is performed, the upward operation wire 32U in the state of being pulled is slackened, so that the operation wire intermediate portion 32a of the upward operation wire 32U is slackened from the state of tightening the annular member 136. Thereby, the diameter of the annular member 136 is elastically increased, so as to prevent the rotation of the pulley 34 from being transmitted. As a result, the bending portion 7 is returned to the linear state. At this time, the operation wire 32 is slackened around the peripheral surface of the annular member 136. However, the operation wire 32 is regulated by the engagement recessed portion 41 of the annular member 136 and the engagement projecting portion 32d of the operation wire 32, so that the operation wire 32 is prevented from being moved with respect to the annular member 136 and from being positionally shifted in the width direction X on the annular member 136. Thereby, it is possible to more surely prevent the operation wires 32 from being rubbed with each other.

Further, in the present embodiment, as described above, the each operation wire 32 is prevented from being moved in the radial direction with respect to the annular member 136 corresponding to the operation wire 32 by the pair of projecting portions 138a and 139a which are the first regulating mechanism portion, and is also prevented from being moved in the peripheral direction C by the engagement recessed portion 41 of the annular member 136 and the engagement projecting portion 32d of the operation wire 32 which are the second regulating mechanism portion. For this reason, there is also an advantage that the operation wire 32 and the annular member 136 can be integrally handled at the time of assembly and disassembly, and that the unit of the bending mechanism 31 is easily attached and detached to and from the endoscope.

Note that in the present embodiment, it is assumed that the first regulating mechanism portion is configured by the pair of the projecting portions 138a and 139a which face with each other by respectively having gaps 138b and 139b. However, the first regulating mechanism portion is not limited thereto.

Figure 17:
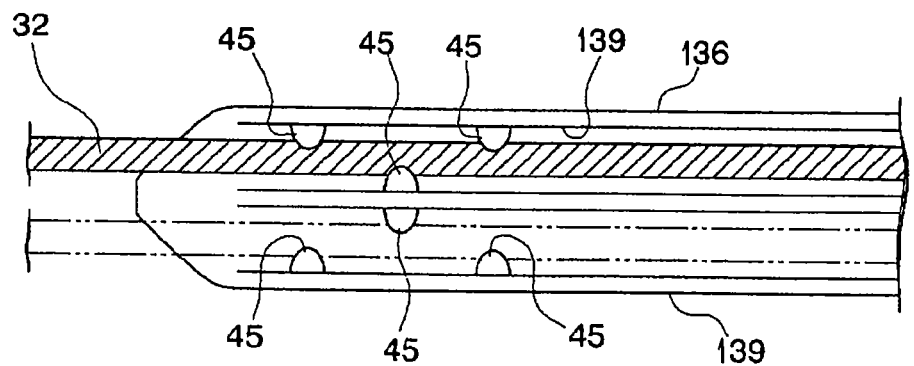
FIG. 17 is a detail view explaining a modification of the annular member and another configuration of the second groove.

FIG. 17 shows a modification of the first regulating mechanism portion, and shows an example provided with the second groove 139. As shown in FIG. 17, in the present modification, the first regulating mechanism portion is configured by three substantially circular projecting portions 145. The three projecting portions 145 are alternatively provided on the both opposing side surfaces of the second groove 139. By alternatively providing the three or more projecting portions 145 on the both side surfaces, it is possible that the operation wire 32 is easily wound and received in the second groove 139, and that in the received state in the second groove 139, the received state is surely maintained so as to prevent the operation wire 32 from being moved to the outside in the radial direction of the annular member 136.

Further, in the present embodiment, it is assumed that the maximum rotation angle at which the annular member 136 can be rotated by the pulling operation member 23 is 90 degrees, and that the winding end position B can be rotated by 45 degrees from the reference line L to the side of the bending portion 7 and can be rotated by 45 degrees from the reference line L to the opposite side. However, the maximum rotation angle $\theta$ can be suitably changed according to the maximum pulling amount of the proximal end side pulled by the pulling operation member 23 and according to the outer diameter of the annular member 136.

However, the rotational movement of the winding end position B is efficiently converted into the component in the pulling direction P by setting the rotation movement range R of total 90 degrees in such a manner that the winding end position B is moved by 45 degrees from the initial position B0 to the reference line L and is moved by 45 degrees from the reference line L to the maximum pulling position B1.

Further, in the present embodiment, it is assumed that four paired sets of the operation wire 32 and the annular member 136 are provided, but the present invention is not limited thereto. The bending portion 7 can be bent to a predetermined direction in correspondence with the number of the operation wires 32 by providing at least the one paired set.

Further, it is assumed that in the annular member 136, the second groove 139 is provided at two places, but the present invention is not limited thereto. When the second groove 139 is provided at least at one place so as to be positionally shifted from the first groove 138 in the width direction X, it is possible to prevent the operation wires from being rubbed with each other.

Further, when the second groove 139 is provided at three places or more, the selectable positions in the width direction X are increased, and thereby a more suitable position can be selected.

Further, the same effect can be expected by providing a plurality of the first grooves 138 in the width direction X in place of the second groove 139.

Note that in the above described embodiments, the endoscope apparatus is described by using an endoscope apparatus configured by an endoscope and an apparatus main body, but the present invention is not limited thereto. For example, the endoscope apparatus may also be configured such that the function of the apparatus main body is incorporated in the side of the endoscope.

Further, in the present embodiment, it is assumed that the annular member 136 which is the rotating body, and the operation wire intermediate portion 32a of the operation wire 32, which is wound around the annular member 136, are rotated by the rotational drive force of the pulley 34, and thereby the distal end portion 32c of the operation wire 32 is pulled so as to bend the bending portion 7, but the present invention is not limited thereto. That is, it may also be configured only such that a rotating body is rotatably provided around the shaft body 34a, and the operation wire intermediate portion 32a of the operation wire 32 is wound around the rotating body. Even in this case, the distal end portion 32c can be pulled by the pulling force of the proximal end portion 32b of the operation wire 32 pulled by the pulling operation member 23 only without the action of the rotational drive force of the pulley 34.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope, comprising:
    an insertion portion having a bendable portion;
    a controller for controlling the movement of the bendable portion, comprising;
        a pulley which is rotatable about a rotational axis;
        a plurality of elastically deformable annular members located at axially spaced positions around the pulley;
        a plurality of pulling members;
        each annular member being associated with a respective one of the pulling members and:
            having a substantially C-Shape including a cut-out; and
            two groove paths, the first groove path including a common first groove and a second groove, the second groove path including the common first groove and a third groove, the second and third grooves being axially spaced from one another and from said first groove such that when the pulling member is placed in the first groove path it enters the first groove at a start position and exits the second groove at a first end position which is axially spaced from the start position and when the pulling member is placed in the second groove path it enters the first groove at the start position and exits the third groove at a second end position which is axially spaced from the start position, the first and second end positions being axially spaced apart;
        each pulling member being located in the first or the second groove path of its associated annular member; and
        each pulling member extending through the first or second groove path of its associated annular member to the bendable portion.

2. The endoscope according to claim 1, further including a motor for driving the pulley.

3. The endoscope according to claim 1, wherein the pulling members are wires.

4. The endoscope according to claim 1, wherein, for each annular member, the first, second and third grooves each extend only part way around the circumference of the annular member of which it is a part.

5. The endoscope according to claim 1, wherein, for each annular member, the second and third grooves are of equal length.

6. The endoscope according to claim 5, wherein, for each annular member, the second and third grooves run parallel to one another.

7. The endoscope according to claim 6, wherein, for each annular member, the second and third grooves are coextensive.

8. The endoscope according to claim 1, wherein, for each annular member, each of the grooves include projecting portions for maintaining the pulling member inside the groove.

9. The endoscope according to claim 1, wherein, for each annular member, the first and second groove paths together form a Y shape.

10. The endoscope according to claim 1, wherein, for each annular member, the second and third grooves are separated by a partition.

11. The endoscope according to claim 1 wherein, for each annular member, each of the first and second groove paths extend less than the full circumference of the annular member.

12. The endoscope according to claim 1, wherein, for each annular member, the pulling member is attached to its annular member in such a manner that the annular member and pulling member move together.

13. The endoscope of claim 12, wherein each annular member is attached to its associated pulling member by the interaction between a projecting portion on the pulling member and a corresponding recessed portion on the outer surface of the annular member.

14. The endoscope according to claim 13, further including an operation member that allows a user of the endoscope to control the movement of the pulling members.

15. The endoscope according to claim 1, wherein the operation member includes a stopping member for holding the pulling members in a fixed position and thereby holding the bendable portion in a fixed position relative to the insertion portion.

16. The endoscope according to claim 15, wherein the operation member includes a control stick which is moveable along a spherical plane and wherein the operation member moves one or more of the pulling members in an upward direction in response to movement of the control stick.

17. The endoscope of claim 16, further including a spherical surface connected to the control stick and movable therewith, the stopping member being brought into contact with the spherical surface to hold the spherical surface, and with it the pulling members in a fixed position.

18. The endoscope of claim 17, wherein the stopping member has a spherical recess that is placed in contact with the spherical surface when the stopping member is brought into contact with the spherical surface.

19. The endoscope according to claim 11, wherein its outer diameter is greater at the end position than at the start position.

20. The endoscope according to claim 19, wherein, for each annular its outer diameter gradually increases from the start position to the end position.

21. The endoscope according to claim 1, wherein each annular member has an inner surface which is normally out of contact with the pulley but can be compressed and placed in contact with the pulley such that the annular member can rotate around the rotational axis along with the pulley.

* * * * *